(12) United States Patent
Sun et al.

(10) Patent No.: US 8,846,379 B2
(45) Date of Patent: Sep. 30, 2014

(54) VISION BASED METHOD FOR MICROMANIPULATING BIOLOGICAL SAMPLES

(76) Inventors: Yu Sun, Toronto (CA); Wenhui Wang, Christchurch (NZ)

(*) Notice: Subject to any disclaimer, the term of this patent is extended or adjusted under 35 U.S.C. 154(b) by 1045 days.

(21) Appl. No.: 12/933,608

(22) PCT Filed: Mar. 19, 2008

(86) PCT No.: PCT/CA2008/000522
§ 371 (c)(1),
(2), (4) Date: Sep. 20, 2010

(87) PCT Pub. No.: WO2009/114922
PCT Pub. Date: Sep. 24, 2009

(65) Prior Publication Data
US 2011/0027885 A1 Feb. 3, 2011

(51) Int. Cl.
*C12M 1/36* (2006.01)

(52) U.S. Cl.
USPC ...................................... 435/286.2

(58) Field of Classification Search
USPC ............................. 435/379, 286.2
IPC ... G02B 21/32; B01L 2300/0829; C12M 23/50; C12N 15/89
See application file for complete search history.

(56) References Cited

U.S. PATENT DOCUMENTS 5,325,289 A * 6/1994 Togawa ............................ 700/61
6,358,749 B1 * 3/2002 Orthman ........................ 436/177

FOREIGN PATENT DOCUMENTS

CA 2560352 3/2008
CN 101598850 * 7/2009

OTHER PUBLICATIONS

Lukkari M. Multi-Purpose Impedance Based Measurement System to Automate Microinjection of Adherent Cells. IEEE International Symposium of Computational Intelligence in Robotics & Automation, Jul. 2005.*
Y. Sun et al, "Biological Cell Injection Using an Autonomous Microbiotic System," Int. J. Robot Res. vol. 21. No. 10-11, pp. 861-868, 2002.
L. Mattos et al, "New Developments Towards Automated Blastocyst Microinjections," in Proc. IEEE International Conference on Robotics and Automation, pp. 1924-1924, 2007.
R. Kumar et al, "Preliminary Experiments in Robot/Human Cooperative Microinjection," Proc. IEEE International Conference on Intelligent Robots and Systems, pp. 3186-3191, 2003.
H. Matsuoka et al., "High Throughput Easy Microinjection with a Single-Cell Manipulation Supporting Robot," J. of Biotechnology, vol. 116, pp. 185-194, 2005.
W.H. Wang, X.Y. Liu, D. Gelinas, B. Ciruna and Y. Sun, "A Fully Automated Robotic System for Microinjection of Zebrafish Embryos," PLos One, vol. 2, No. 9, p. e862 Sep. 2007.
S. Zappe et al, "Automated MEMS-based *Drosophilia* Embryo Injection System for High-Throughput RNAi Screens," Lap Chip, vol. 6, pp. 1012-1019, 2006.
Lukkari et al, Proc. 2005 IEEE International Symposium on Computational Intelligence in Robotics and Automation, pp. 701-706, Jun. 27-30, 2005.
D.L. Applegate et al, "The Travelling Salesman Problem: A Computational Study," Princeton University Press, 2006, Chapters 1 and 15.
Mark De Berg, Marc Van Kreveld, Mark Overmars and Otfried Schwarzkopf, Computational Geometry, 2nd Edition, Springer-Verlag, 2000, Chapter 9.
Wang et al "Autonomous Zebrafish Embryo Injection Using a Microbiotic System," 3rd Annual IEEE Conference on Automation Science and Engineering, pp. 363-368, Sep. 2007.

* cited by examiner

*Primary Examiner* — Ralph Gitomer
(74) *Attorney, Agent, or Firm* — Eduardo Krupnik; Miller Thomson LLP (57) ABSTRACT

A system and method for micromanipulating samples are described to perform automatic, reliable, and high-throughput sample microinjection of foreign genetic materials, proteins, and other molecules, as well as drawing genetic materials, proteins, and other molecules from the sample. The system and method overcome the problems inherent in traditional manual micromanipulation that is characterized by poor reproducibility, human fatigue, and low throughput. The present invention is particularly suited for adherent cell microinjection but can be readily extended to aspiration, isolation, and electrophysiological measurements of microorganisms, unicellular organisms, or cells.

11 Claims, 13 Drawing Sheets

VISION BASED METHOD FOR MICROMANIPULATING BIOLOGICAL SAMPLES

CROSS REFERENCE TO RELATED APPLICATIONS

The present application is a national stage application under 35 U.S.C. 371 of International Application No. PCT/CA2008/000522 filed Mar. 19, 2008, the contents of which are hereby incorporated by reference into the present disclosure.

FIELD OF THE INVENTION

The present invention relates to micromanipulation, automation, computer vision, and microrobotics, and more specifically to a system and method for micromanipulating samples, such as microorganisms and cells.

BACKGROUND OF THE INVENTION

The micromanipulation of microorganisms, including unicellular and multicellular microorganisms and cells permits the insertion of foreign materials into individual cells for genetic manipulation, cellular response quantification, or intracellular structure imaging. Possessing many advantages, mechanical cell injection is highly effective for delivering macromolecules and is free from concerns about phenotype alteration.

As cell injection is a labor intensive task, efforts for automating cell injection have been continuous. The vast majority of these systems were developed to facilitate the handling of mouse/Drosophila/zebrafish embryos/oocytes for genetics and reproduction applications (See Y. Sun and B. J. Nelson, "Biological cell injection using an autonomous microrobotic system," Int. J. Robot. Res., Vol. 21, No. 10-11, pp. 861-868, 2002; L. Mattos, E. Grant, R. Thresher, and K. Kluckman, "New developments towards automated blastocyst microinjections," in Proc. IEEE International Conference on Robotics and Automation (ICRA'2007), 2007; R. Kumar, A. Kapoor, and R. H. Taylor, "Preliminary experiments in robot/human cooperative microinjection," Proc. IEEE International Conf on Intelligent Robots and Systems, pp. 3186-3191, Las Vegas, 2003; and H. Matsuoka, T. Komazaki, Y. Mukai, M. Shibusawa, H. Akane, A. Chaki, N. Uetake, and M. Saito, "High throughput easy microinjection with a single-cell manipulation supporting robot," J. of Biotechnology, Vol. 116, pp. 185-194, 2005; W. H. Wang, X. Y. Liu, D. Gelinas, B. Ciruna, and Y. Sun, "A fully automated robotic system for microinjection of zebrafish embryos," PLoS ONE, vol. 2, no. 9, p. e862, September 2007; and S. Zappe, M. Fish, M. P. Scott, and O. Solgaard, "Automated MEMS-based drosophila embryo injection system for high-throughput RNAi screens," Lap Chip, Vol. 6, pp. 1012-1019, 2006).

In microrobotic injection of suspended cells (e.g., embryos/oocytes), cells must be immobilized, preferably into a regular pattern to minimize cell searching and switching tasks and increase injection speed. Differently, most mammalian cells (e.g., HeLa cells, fibroblasts, and endothelial cells) adhere to the bottom surface of a culture dish/plate during in vitro culture into an irregular pattern. Although adherent cells do not require immobilization efforts, they are highly irregular in morphology, which makes robust pattern recognition difficult and full automation challenging. Additionally, they are only a few micrometers thick, posing more stringent requirements in microrobotic positioning. The small thickness and large variations require precise determination of relative vertical positions between the micromanipulating device and the cell.

A microinjection system for microinjecting adherent cells is disclosed in Lukkari et al (Proc. 2005 IEEE International Symposium on Computational Intelligence in Robotics and Automation). The micromanipulator of the system, however, is a joystick-controlled semi-automatic device that necessitates an operator to control movement of an injecting device and the microinjection of the cells. Hence, the semi-automatic system of this disclosure is immune to operator proficiency variations and from human fatigue.

Currently, no automated, high-throughput adherent cell micromanipulation systems are known. Such automated systems can serve as an important tool in the biotech industry and will have significant implications in molecule testing and the creation of stem cell lines for individualized stem cell-based therapy.

In view of the foregoing, what is needed is a system and method for cellular micromanipulation that overcomes the limitations of the prior art, such that the system and method is capable of automation, provides robustness, high-throughput (including sample positioning), high success rates, and high reproducibility.

SUMMARY OF THE INVENTION

Briefly described, one aspect of the present invention is a method for micromanipulation of a plurality of samples, said method comprising: providing a system for micromanipulating samples, the system including: a microscopic means, a micromanipulating means having a tip, a positioning device to control motion of the tip and means for determining a shortest path along the plurality of samples, determining a home point for the tip, establishing a shortest path along the plurality of samples, and moving the tip by means of the positioning device from the home point to the samples and micromanipulating the samples in sequence along the shortest path.

In another aspect, the method of the present invention further comprises selecting destination targets in the plurality of samples and micromanipulating the plurality of samples in sequence along the shortest path at the destination targets.

One aspect of the present invention is a system for the micromanipulation of samples in a container, the system comprising: a positioning device operable to control motion of a tip of a micromanipulating means, a microscopic means and a means for generating the shortest path along the samples, wherein the system is operable to micromanipulate the samples in sequence along the shortest path.

In one aspect of the present invention, the system further comprising a pattern recognition means to select a destination target within the samples, wherein the system is operable to micromanipulate the samples at the destination target in sequence along the shortest path.

The present invention overcomes the problems of poor reproducibility, human fatigue, and low throughput inherent with traditional manual adherent cell micromanipulation techniques. Advantages of the present invention also include automating sample micromanipulation high reproducibility, and genuine high-throughput biological research.

BRIEF DESCRIPTION OF THE DRAWINGS

A detailed description of the preferred embodiments is provided herein below by way of example only and with reference to the following drawings, in which.

In the drawings, one embodiment of the invention is illustrated by way of example. It is to be expressly understood that the description and drawings are only for the purpose of illustration and as an aid to understanding, and are not intended as a definition of the limits of the invention.

DETAILED DESCRIPTION OF THE INVENTION

The system and methods of the present invention are designed for the micromanipulation of samples.

The term "samples" as used herein refers to any object suited for micromanipulation. Without limitation, samples include unicellular and multicellular microorganisms, cells (animal and plant cells), and bacteria.

The term "micromanipulation" as used herein includes, without limitation, microinjection of a substance or material into a sample, aspiration or withdrawal of substances or materials from a sample, sample isolation and electrophysiological (electrical) measurements.

Figure 1:
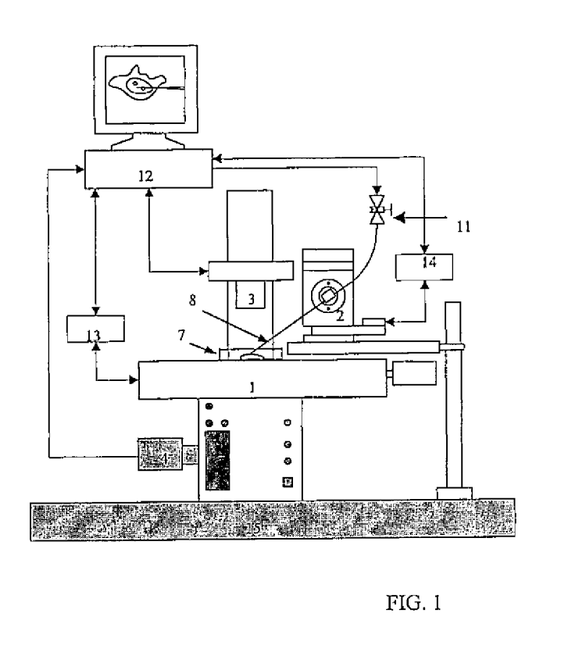
FIG. 1 illustrates a schematic diagram of components of the automated adherent cell injection system.

With reference to FIG. 1, a system in accordance with one aspect of the present invention includes a microscopic means 3, micromanipulating means 8 having a tip, a positioning device 2 to control motion of the tip and means for determining a shortest path along the plurality of samples.

In one aspect of the present invention, a positioning control device 14 is included to physically provide control signals to the positioning device 2.

The micromanipulating means 8 can be embodied as an injection micropipette 8 (glass capillary or microfabricated needle) attached to the positioning device 2. For microinjecting embodiments, the tip of the micropipette 8 is within 1 μm in outer diameter.

The microscopic means 3 can be embodied as an inverted optical microscope 3.

In another aspect, the system of the invention may further comprise:

a) Utilities running on a computer 12 for motion control and image processing. The utilities include, without limitation, an interactive control program interface. Motion control may be provided by a control utility, provided in a manner that is known, to enable the control functions described herein. Image processing may be provided by means of an image processing means or utility, also provided in a manner that is known, to enable image processing in support of the control functions as described herein. The image processing utility, in one implementation, is linked to the camera described below and is thereby operable to capture an image corresponding to the field of view of the microscope means, and enables a user by operation of the computer to interact with one or more resulting images for the purpose of optionally manually selecting target(s); reviewing the results of automatic target selection as described; and optionally manually adjusting the target(s) selected. The image processing utility is linked to or includes the pattern recognition means so as to enable automatic target selection as described.

Figure 7:
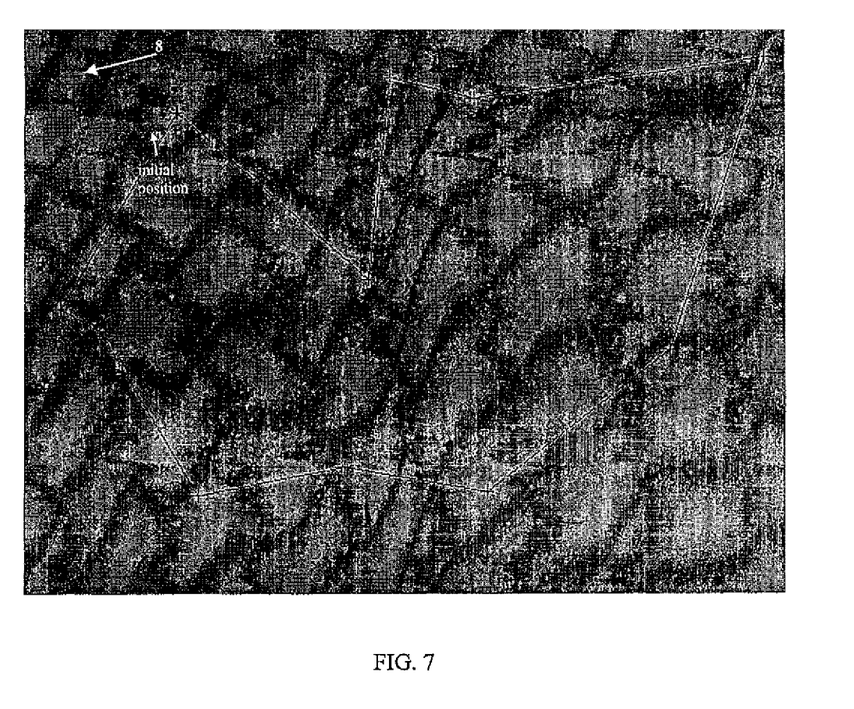
FIG. 7 illustrates an example showing the shortest injection path for the system to inject a number of cells. Each deposition destination represents a node.

In addition, the control utility and the image processing utility are linked so as to enable the control utility to utilize images captured by operation of the image processing utility for example for the purpose of determining the shortest path between selected targets or between the samples (for example), and then displaying an image that includes the results of the determination of the shortest path, as shown in FIG. 7.

b) A positioning means 1, such as a multi-DOF motorized positioning stage or microrobots that control the motion of a sample container.

c) A sample container 7 placed on positioning means 1. Sample container 7 can be embodied as a Petri dish, glass slide, PDMS device, or containers made of other transparent, biocompatible materials with a uniform and flat bottom surface. Sample container 7 may contain one or a plurality of samples.

d) A computer-controlled pressure unit 11.

e) A vibration isolation table 15 to minimize vibration.

f) A CCD/CMOS camera 4 mounted on the microscopic means 3.

Figure 2:
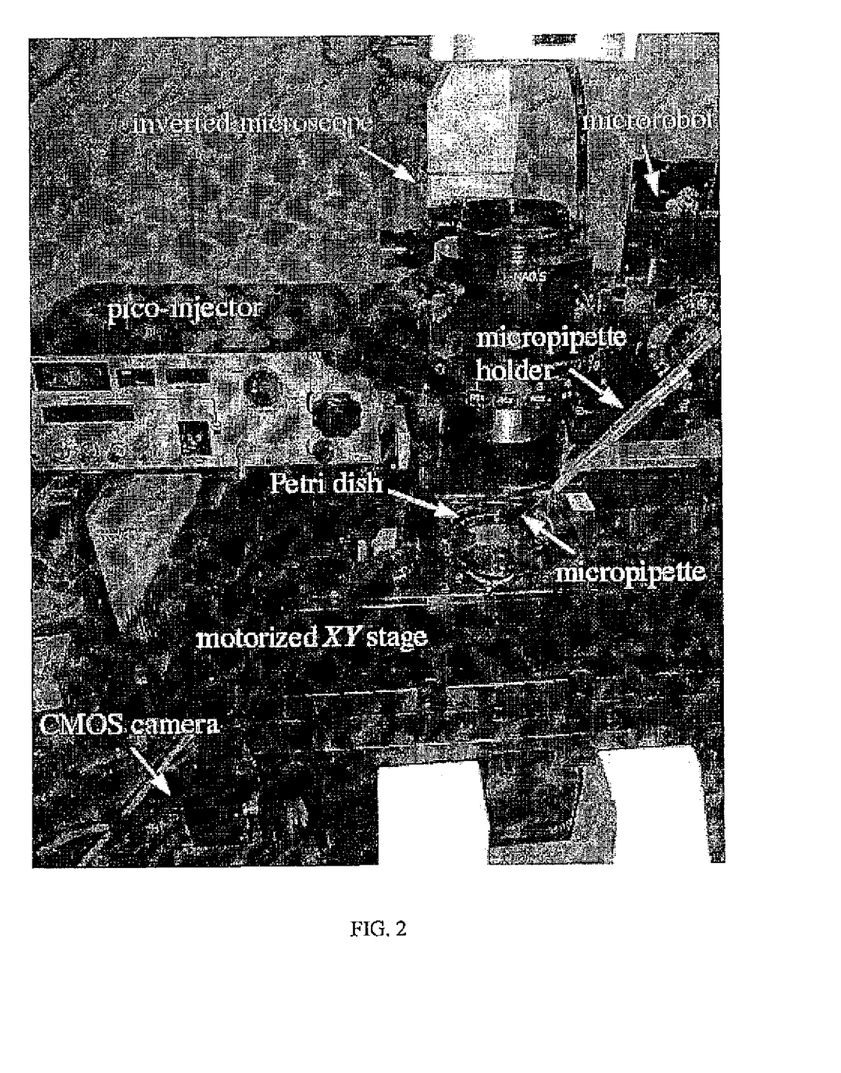
FIG. 2 illustrates an example system setup.

FIG. 2 shows an example system setup. Although this particular configuration of the system relates to the microinjection of material into endothelial cells, it should be expressly understood that this is an illustrative example only and the present invention is directly applicable for the automated micromanipulation of samples as would be recognized and understood by a person of skill in the art.

Figure 3:
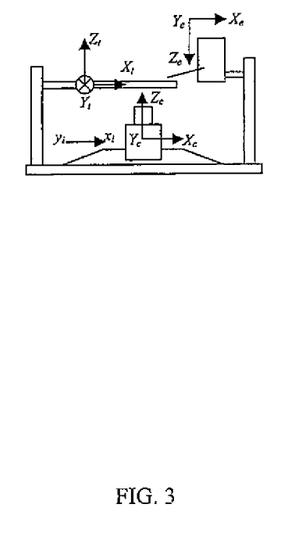
FIG. 3 illustrates coordinate frames in the present invention.
Figure 4:
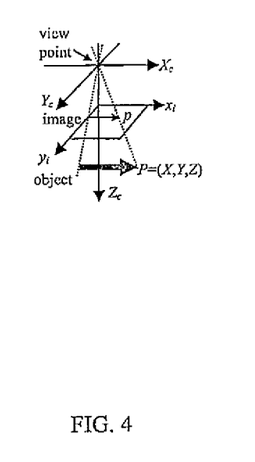
FIG. 4 illustrates an image projection model relating camera/image frames.

The coordinate frames of the system used in FIG. 3 and FIG. 4 are summarized in Table 1.

TABLE 1

Coordinate frames (FIG. 3 and FIG. 4) of the system.

| Symbol | Coordinate frame |
|---|---|
| e | End-effector coordinate frame $X_e$-$Y_e$-$Z_e$ attached to positioner 2 (micromanipulating means 8 as the end-effector) |
| t | Target coordinate frame $X_t$-$Y_t$-$Z_t$ attached to positioner 1 that controls the motion of cells |
| c | Camera coordinate frame $X_c$-$Y_c$-$Z_c$ |
| i | Coordinate frame $x_i$-$y_i$ (or x-y) for the image plane |

A point P=(x, y, z) in the camera frame $X_c$-$Y_c$-$Z_c$ is mapped to a point p=(u,v) in the image plane x-y via $$\begin{bmatrix} s_x & 0 \\ 0 & s_y \end{bmatrix} \begin{bmatrix} u \\ v \end{bmatrix} = \begin{bmatrix} x \\ y \end{bmatrix}$$

where $s_x$ and $s_y$ are fixed scale factors or pixel size in x-axis ($s_x$) and y-axis ($s_y$) respectively that can be either calibrated off-line manually or on-line automatically as discussed later. They will be referred to as s thereafter.

Overall Micromanipulation Method

A method for the micromanipulation of a plurality of samples according to the present invention includes:
(a) providing a microscopic means 3, a micromanipulating means 8 having a tip, a positioning device 2 to control motion of the tip and means for determining a shortest path along the plurality of samples;
(b) determining a home point for the tip;
(c) establishing a shortest path along the plurality of samples; and moving the tip by means of the positioning device 2 from the home point to the samples and micromanipulating the samples in sequence along the shortest path.

Although the aspect of the method described in this section relates to the microinjection of material into endothelial cells, it should be expressly understood that the present invention is directly applicable for the micromanipulation of samples as would be recognized and understood by a person of skill in the art.

A large number of endothelial cells are seeded on the surface of cell container 7. The cells in the container 7 are brought into focus, for example using a known auto-focusing algorithm, and viewed with the microscopic means. The vertical position of the micropipette 8 tip is viewed, for example with a vision-based contact detection algorithm. Destination targets within the cells under the field of view ("cell segment") are recognized through pattern or cell recognition means and selected. A shortest injection path is generated based on the destination targets. Along the shortest path, the micropipette tip penetrates the membrane of each target cell and deposits a pre-specified amount of any material of interest into all the target cells sequentially at approximately the destination target. Upon the completion of injecting all the cells within the cell segment, the next cell segment is then brought into the field of view. The cells are recognized, the shortest path is generated, and injection process is repeated for all segments on the cell container.

Micropipette Motion Control Sequence for Infecting Each Cell

Figure 5:
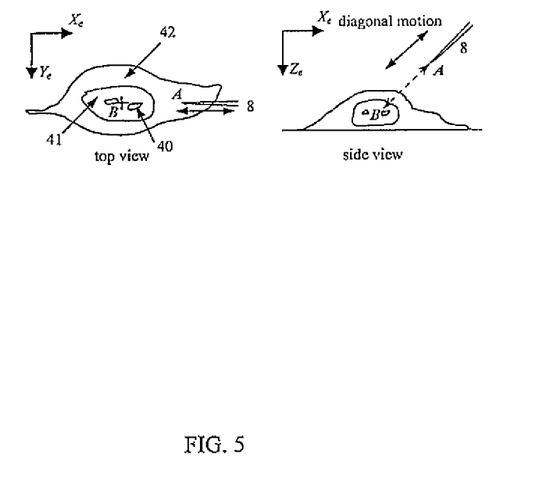
FIG. 5 illustrates micropipette motion pattern for injecting each adherent cell.

As shown in FIG. 5, the micropipette 8 tip moves along its diagonal direction. The motion sequence of the micropipette 8 for injecting a cell is as follows:
1. Move micropipette 8 to home point A simultaneously in $X_e$-$Y_e$ plane with positioner 2.
2. Penetrate the cell membrane and move to the destination target B in nucleus along its diagonal direction. Upon reaching destination target B, a pre-specified amount of genetic materials is deposited by the computer-controlled pressure unit 11.
3. Retreat from destination target B along its diagonal direction back to home point A.

The deposition destination or destination target can be, without limitation, inside the cell, such as in the nucleus or cytoplasm or on the cell membrane. The present invention allows for precise, highly reproducible micromanipulation of cells at either nucleus or cytoplasm or other cytoplasmic organelles.

Figure 6:
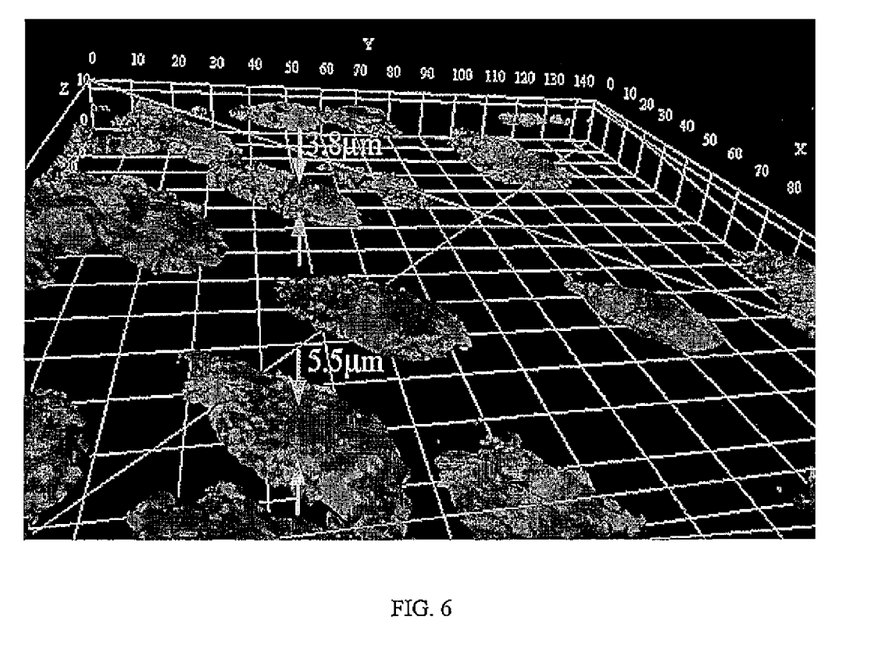
FIG. 6 illustrates 3-D profile of endothelial cells. Reconstructed from a stack of confocal fluorescence images.

For a given cell type, its height can be measured by measuring means such as by confocal imaging. Referring to FIG. 6, the endothelial cells used in this embodiment range from 3.8 to 5.5 µm in height. Thus, in this example the home point A may be defined as 8 µm above the container surface, while destination target B is defined as 2 µm above the container surface. Points A and B are collinear with the micropipette diagonal axis and have a distance of octan($\alpha$)µm along the $X_e$ axis, where $\alpha$ is the tilting angle of the micropipette with respect to the container surface. $X_e$-coordinate of home point A=[$X_e$-coordinate of destination target B+octan($\alpha$)]µm, $Y_e$-coordinate of home point A=$Y_e$-coordinate of destination target B.

Shortest Injection Path

The cell recognition results provide destination targets B for each cell, producing an array of destination points with x- and y-coordinates in the image plane. Coordinates in the image plane are on-line transformed to $X_e$- and $Y_e$-coordinates according to the defined coordinate frames. Including the initial position of the micropipette, a shortest injection path is generated, such as using the classical traveling salesman algorithm (See D. L. Applegate, R. E. Bixby, V. Chvtal, and W. J. Cook, "The traveling salesman problem: A computational study." Princeton University Press, 2006). As shown in FIG. 7, the injection sequence can either be clockwise or counter-clockwise.

If desired, the destination points can be alternatively specified manually by an operator through interactive input (e.g., through computer mouse clicking).

Injection Control Flow

Figure 8:
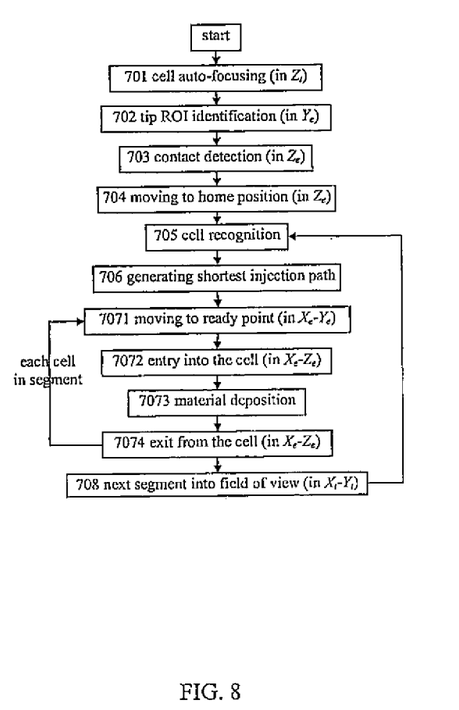
FIG. 8 illustrates automatic injection control flow.

The control flow of automated adherent cell injection is described in FIG. 8.

Cell Auto-Focusing 701:

Prior to injection, the cells need to be brought into focus. Movement of cells in the container are controlled by positioner 1 upwards (or downwards) through a certain distance (e.g., 20 µm) to cross the focal plane. An autofocusing algorithm (e.g., Tenenbaum gradient) is used to locate the focal plane by constantly calculating the focus measure for each frame of image. The cells are moved to the focal plane that corresponds to the maximum (or minimum) focus measure. Depending on the unevenness of the container surface (commercial Petri dishes commonly used in a biology laboratory is found to often vary by 1-2 µm even within a small neighbourhood), this auto-focusing step 701 may need to be repeated for each cell segment.

Identification of Micropipette Tip ROI (Region of Interest) 702.

Figure 9:
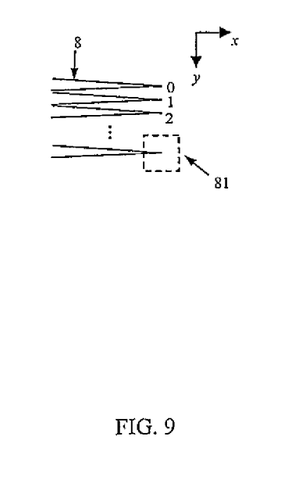
FIG. 9 illustrates a micropipette moving in the image plane.

This step is to locate the tip of the micropipette 8 for use in contact detection 703. The micropipette 8 controlled by positioner 2 moves only along the $Y_e$ direction. The moving micropipette that stands out in the image subtracted from the background is recognized (i.e., a region of interest 81 around the tip of the micropipette, shown in FIG. 9 is identified). Upon identification, the coordinates of the tip both in the image plane x-y and in the end-effector frame $X_e$-$Y_e$-$Z_e$ are determined. The x-coordinate and y-coordinate in the image plane x-y, $X_e$-coordinate and $Y_e$-coordinate in the end-effector frame $X_e$-$Y_e$-$Z_e$ are taken as the lateral components of the home position of the micropipette tip.

Figure 10:
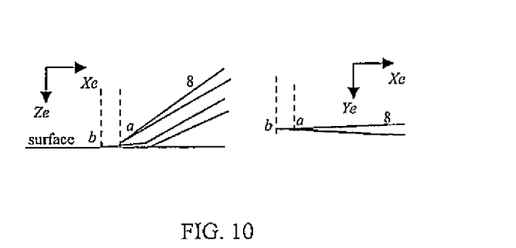
FIG. 10 illustrates contact between micropipette tip and bottom surface of a cell dish.

Contact Detection 703 Using Computer Vision Feedback:

This step is to automatically align the tip of the micropipette 8 with the destination target B in the vertical direction. In this procedure, the top surface of the cell holding device 7 where the cells are seeded serves as the reference plane. The micropipette 8 moves only along the $Z_e$ direction. Upon the establishment of the contact between the micropipette tip and the top surface, further vertical motion of the micropipette tip along the $Z_e$ direction results in lateral movement along the $X_e$ direction. As shown in FIG. 10, the micropipette tip is located at point a (initial contact) and b (after contact) in the surface plane. Before and after contact, the micropipette tip changes its x coordinate in the image plane x-y vs. time (i.e., image frame number), resulting in a V-shaped curve. The peak of the V-shaped curve represents the contact position along the vertical direction between the micropipette tip and the top surface of device 7.

The $Z_e$-coordinate of the home position of the micropipette 8 tip is determined by moving upwards with respect to the contact position by more than the cell height, i.e., 8 μm for endothelial cells.

Upon the completion of 702 and 703, the home position of the micropipette tip both in the x-y image plane and the $X_e$-$Y_e$-$Z_e$ frame has been automatically determined and will be fixed for use in the following procedures of injecting all cells within the segment.

Moving to the Home Position 704.

After 702 and 703, positioner 2 following a position control law (e.g., PID) moves the micropipette 8 tip upwards to its home position determined in 702 and 703 from the vertical contact position in order to prevent the micropipette 8 from crashing with cells in between injections.

Cell Recognition 705:

The task of this step is to identify cell structures or targets (i.e., nucleus 41 and cytoplasm 42). The cell recognition steps are summarized in Table 2. The identification of targets within the cells may be done manually or automatically.

TABLE 2

| Cell recognition 705. | |
|---|---|
| Step # | Processing |
| 1 | Nucleolus 40 recognition |
| 2 | Nucleus 41 recognition |
| 3 | Cytoplasm 42 recognition |

An example recognition process can be as follows:

(1) Nucleolus 40 recognition. A gray-level template containing a single nucleus is used to locate all nucleoli in the image of the current cell segment, using a template matching method.

(2) Nucleus 41 recognition. All recognized nuclei are clustered with each cluster containing a single nucleus or two nuclei. Circumscribing a cluster, a circle is virtually specified as the initial points for 'snakes', which form a closed curve representing the contour of nucleus envelope. The centroid of the contour is recognized as the nucleus center B.

(3) Cytoplasm 42 recognition. In between nucleus contours is cytoplasm, from which deposition destinations beyond nucleus can be selected.

Figure 12:
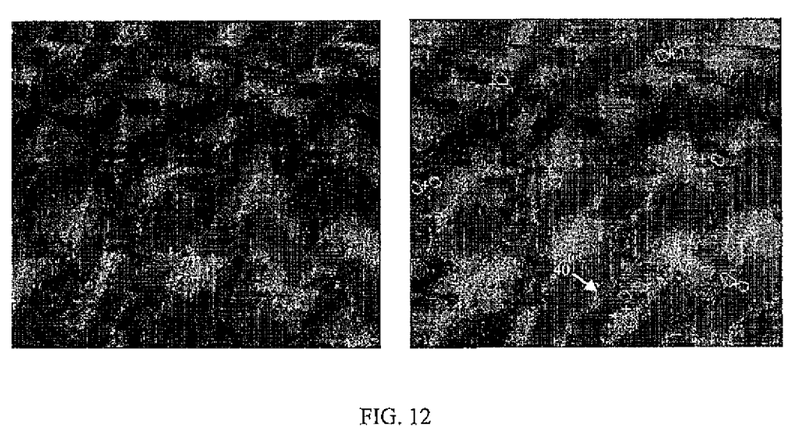
FIG. 12 illustrates an example showing nucleoli cell recognition.

Another example recognition process can be as follows:

Nucleoli 40 recognition. With reference to FIG. 12, an original image is normalized to make all pixels in the image have an intensity between 0 and 255 in order to increase image contrast. Based on the normalized image, for the fixed configuration, two thresholds, T1 and T2, are specified to distinguish the light surface and dark shadow regions of nucleoli. Pixels with an intensity>T1 are classified as the light surface regions, and neighbouring pixels with intensity<T2 in one particular direction of the light surface regions are classified as the dark shadow regions.

The pairs of light and dark regions are then considered to be candidate nucleoli, which are checked against a set of criteria before being identified as nucleoli, as outlined in FIG. 9b. These criteria include:

The area is large enough but not too large (i.e., 80<Area<500, measured in pixels).

The smallest distance in the x or y direction is no smaller than one tenth of the largest distance in the opposite direction.

The dark shadow is in the right direction with respect to the light region within a tolerance.

The dark and light regions are about the same size within a factor of 2.

The dark region is not simply a vertical or horizontal line (which would indicate a ridge).

The candidate nucleolus does not have more than 5 neighboring candidate nucleoli.

Based on the recognized nucleoli, Delaunay triangulation (Mark de Berg, Marc van Kreveld, Mark Overmars, and Otfried Schwarzkopf, Computational Geometry, 2nd edition, Springer-Verlag. 2000) is used to find close nucleoli which stays inside one nucleus. A virtual circle centered at the centroid of the nucleoli with radius of 100 pixels is constructed as the initial curve for 'snakes', which will form a closed curve that represents the contour of nucleus.

For selecting a destination target inside the nucleus: For the nuclei containing more than one nucleolus, the centroid of the nucleoli can be selected as the destination target in nucleus to minimize diffusion paths. For nuclei containing only one nucleolus, the centroid of the nucleus can be selected as the deposition destination. The '+'s in FIG. 12 represent a set of selected destinations.

For selecting a destination target outside nucleus, in cytoplasm: A point 10-20 pixels away from the nucleus contour can be selected as the deposition destination.

Generating Shortest Injection Path 706:

x- and y-coordinates of the micropipette 8 tip and all the nuclear centers of the recognized cells in the cell segment are input to the traveling salesman problem algorithm to generate a shortest injection path, along which sequential injection is conducted. Each cell is injected according to the procedures 7071-7074.

Moving the Micropipette Tip to Ready Point 7071:

From its resting position, the micropipette 8 is moved by positioner 2 to the home point A by a position control law (e.g., PID).

Entry into the Cell 7072:

The micropipette tip is controlled to start from the home point A to reach the destination point B by a position control law at an appropriate speed without causing cell lysis.

Material Deposition 7073:

Based on a desired deposition volume, the micropipette tip size (inner diameter) and specified injection pressure level determine the positive pressure pulse length (i.e., pressure 'on' time). Injection pressure is maintained high for the determined time period through the computer-controlled pressure unit 11, precisely depositing a desired volume of materials at the destination point B.

Exiting from the Cell 7074:

Controlled by positioner 2, the micropipette 8 is retracted out of the cell by a position control law at an appropriate speed that does not cause cell lysis.

Repeating 7071-7072-7073-7074 to inject each cell in the whole cell segment in sequence along the shortest path.

After injecting one cell segment, the next segment is brought into the field of view. The system repeats injection according to 705-706-7071-7072-7073-7074.

Moving the Next Cell Segment into the Field of View 708:

This step brings the next cell segment into the field of view (the image plane x-y). Positioner 1 moves the cell container by traveling fixed relative displacements along $x_t$ and $Y_t$.

An Alternative Injection Control Flow

Figure 11:
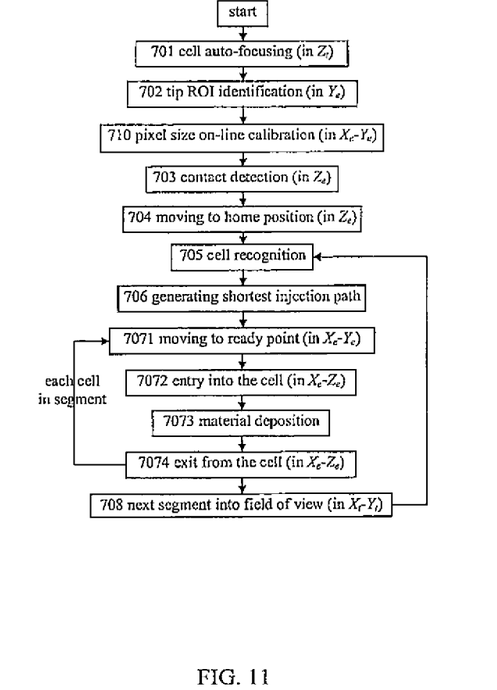
FIG. 11 illustrates alternative injection control flow with an on-line pixel size calibration step.

The control flow described in FIG. 8 requires a prior knowledge of pixel size s that is obtained through off-line pixel size calibration. The pixel size s varies with different microscopy magnifications that are typically determined by microscope objectives, couplers, and the camera. In order to eliminate the magnification/hardware dependence, on-line calibration can be conducted with a visual tracking means to automatically determine the pixel size. The visual tracking means is best understood an aspect of the image processing utility described above that enables the visual markers indicating targets for micromanipulation and/or shortest path information to be visible to a user regardless of different microscopy magnifications by adjusting the pixel size of the markers. Accordingly, the control flow is modified as shown in FIG. 11.

On-Line Calibration of Pixel Size 710:

After identification of the tip, the x- and y-coordinates of the tip in the image plane are determined. Before contact detection, positioning device 2 moves micropipette tip in $X_e$-$Y_e$ plane by a known distance, e.g., 50 μm on both axes. During the course of motion, the tip is selected as the image feature for tracking and a visual tracking method (e.g., sum-squared-difference) is applied. Based on the visual tracking results (i.e., pixel displacement in the image plane x-y) and the travelling distance in the plane $X_e$-$Y_e$, the pixel size s is calibrated on line. The micropipette 8 tip is moved back to its initial position by the known distance on both axes.

It will be appreciated by those skilled in the art that other variations of the aspects of this invention may also be practised without departing from the scope of the invention.

The following non-limiting example is illustrative of the present invention:

EXAMPLE 1

A. Materials

The cells: porcine aortic endothelial cells, isolated from porcine aorta and cultured in cell medium (M199 medium, 5% calf serum, and 5% fetal bovine serum with a pH value of 7.4). Microbotic injection was performed after 2 or 3 days of cell passage.

During system testing, fluorescent dyes (dextran, Texas Red, 70,000 MW, neutral, Invitrogen) mixed with PBS buffer.

The system, used in this example is the system shown in FIG. 2, which employs a three-degrees-of-freedom microrobot (MP-285, Sutter) with a travel of 25 mm and a 0.04 μm positioning resolution along each axis. One motion control card (NI PCI-6289) is mounted on a host computer (3.0 GHz CPU, 1 GB memory) where control algorithms operate. Visual feedback is obtained through a CMOS camera (A601f, Basler) mounted on an inverted microscope (IX81, Olympus). A Polystyrene Petri dish (55 mm, Falcon) where the endothelial cells are seeded is placed on a motorized precision XY stage (ProScanII, Prior). A glass micropipette, heated and pulled using a micropipette puller (P-97, Sutter), is connected to the microrobot via a micropipette holder. The micropipette is tilted 45° C. with respect to the XY stage. A computer-controlled pico-injector (PLI-100, Harvard Apparatus) with a femto-liter resolution provides positive pressure for material deposition. All units except the host computer and pressure unit are placed on a vibration isolation table.

B. Results

Figure 13:
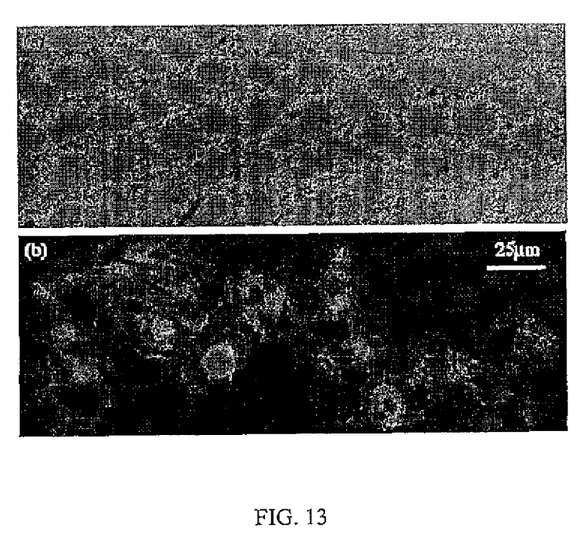
FIG. 13 illustrates an example showing cells microinjected with fluorescent dyes.

The system injected a total of 1012 endothelial cells, demonstrating an operation speed of 25 cells/minute. Cytoplasm instead of nucleus was selected as injection destination target for each cell. The injected cells were inspected under a fluorescence microscope (IX81, Olympus), excited by 540 nm laser light and observed through a TRITC filter set. Visual inspection was conducted right after injection. FIG. 13 shows microrobotically injected endothelial cells under both brightfield (FIG. 13(*a*)) and fluorescence microscopy (FIG. 13(*b*)). The deposited fluorescent dyes (high-brightness) can be clearly observed in the cells. Normal cell morphology is maintained after injection.

To quantitatively evaluate the performance of the microrobotic adherent cell microinjection system, two measures were defined. (1) Survival rate: This measure is defined as the ratio between the number of live cells after injection and the total number of cells injected, essentially representing the severity and frequency of cell damage from injection. Based on the 1012 injected endothelial cells, the microrobotic injection system produced a survival rate of 96%, which was determined through Trypan blue exclusion testing of cell viability. (2) Success rate: This measure is defined as the ratio between the number of cells with materials successfully deposited inside the cell and the total number of injected cells. Essentially, this measure represents the reliability and the reproducibility of the system. Visual inspection revealed that the success rate of the 1012 injected endothelial cells was 82%.

The system is immune from large variations in performance since efforts from operator intervention are trivial (computer mouse clicking) without causing human fatigue as in manual injection. Additionally, the system has a high degree of performance consistency, independent of proficiency differences across operators.

What is claimed is:

1. A method for automated micromanipulation of samples in a container, the method comprising:
   (a) placing the container having the samples under a microscopic means in a system for micromanipulating samples, the system including: a microscopic means, no more than one camera mounted on the microscopic means, a micromanipulating means having a tip, a positioning device to control motion of the tip, means for determining a shortest micromanipulation path along the samples in the container, and processing means operatively linked to the microscopic means, the no more than one camera, micromanipulating means and the means for determining the shortest micromanipulation path long the samples;
   (b) the processing means automatically obtaining images of the tip of the micromanipulating means and the container having the samples using the no more than one camera;
   (b) the processing means automatically using the images of the tip taken by the no more than one camera for determining a home point for the tip;
   (c) automatically establishing the shortest micromanipulation path along the samples using the means for determining the shortest micromanipulation path; and
   (d) the processing means automatically moving the tip by means of the positioning device and micromanipulating the samples in sequence along the shortest micromanipulation path.

2. The method of claim 1, wherein the method further comprises the processing means automatically selecting destination targets in the samples and micromanipulating the samples in sequence along the shortest micromanipulation path at the destination targets.

3. The method of claim 1, wherein the home point is established automatically according to the following steps:
   (i) the processing means using the images taken by the no more than one camera to identify the position of the tip of the micromanipulating means relative to a surface of the container where the samples are placed;
   (ii) the processing means automatically lowering the tip to a contact position with the surface of the container; and
   (iii) the processing means automatically raising the tip substantially vertically with respect to said contact position to a point that is above the height of the samples, such point defining the home point.

4. The method of claim 1, wherein the processing means includes or is linked to a control utility and an image processing utility.

5. The method of claim 2, wherein the destination targets in the samples are selected automatically using a pattern recognition means included or linked to the processing means.

6. The method of claim 1, wherein the samples are adherent cells.

7. The method of claim 5, wherein the samples are cells and the pattern recognition means is operable to recognize one or more of nuclei, nucleoli and cytoplasm in the cells.

8. The method of claim 1, wherein the system further comprises a positioning means to control motion of the sample container.

9. The method of claim 1, wherein said micromanipulation includes microinjecting a substance or material into the samples, aspirating or withdrawing of substances or materials from the samples, isolating the samples and electrophysiological measuring the samples.

10. A method for micromanipulation of adherent cells, wherein said method comprises:
 (a) placing a container having a plurality of adherent cells under a microscopic means;
 (b) obtaining images of the plurality of adherent cells and images of a micromanipulating means using no more than one camera linked to the microscopic means, said micromanipulating means having a tip;
 (c) establishing a home point for the tip using the images of step (b);
 (d) generating a shortest micromanipulation path along the plurality of adherent cells in the container using the images of step (b); and
 (e) moving the tip from the home point to the plurality of adherent cells and micromanipulating the plurality of adherent cells in sequence along the shortest micromanipulation path,
 wherein said images, said home point, said shortest path, and said moving of the tip and micromanipulation are obtained, established, generated or performed automatically by a computer linked to the microscopic means, the no more than one camera and the micromanipulating means.

11. The method of claim 10, wherein said micromanipulating the plurality of adherent cells comprises automatically microinjecting a desired volume of substances or materials into the adherent cells or automatically aspirating a desired volume of substances or materials from the plurality of adherent cells, wherein said desired volume is selected using a computer-controlled pressure unit connected to the micromanipulating means.

* * * * *